US008758788B2

(12) United States Patent
Bruns et al.

(10) Patent No.: US 8,758,788 B2
(45) Date of Patent: Jun. 24, 2014

(54) FUNGICIDALLY ACTIVE COMPOUND COMBINATIONS

(75) Inventors: Rainer Bruns, Leverkusen (DE);
Martin Kugler, Leichlingen (DE);
Thomas Jaetsch, Cologne (DE)

(73) Assignee: Bayer Intellectual Property GmbH, Monheim (DE)

( * ) Notice: Subject to any disclaimer, the term of this patent is extended or adjusted under 35 U.S.C. 154(b) by 750 days.

(21) Appl. No.: 12/691,816

(22) Filed: Jan. 22, 2010

(65) Prior Publication Data

US 2010/0184757 A1 Jul. 22, 2010

Related U.S. Application Data

(63) Continuation of application No. 11/977,086, filed on Oct. 23, 2007, now abandoned, which is a continuation of application No. 10/688,466, filed on Oct. 17, 2003, now abandoned.

(30) Foreign Application Priority Data

Oct. 17, 2002 (DE) .................................. 10 248 335

(51) Int. Cl.
| | | |
|---|---|---|
| *A61K 31/41* | (2006.01) | |
| *A61K 31/5375* | (2006.01) | |
| *A01N 43/653* | (2006.01) | |
| *A01N 43/78* | (2006.01) | |
| *A01N 37/34* | (2006.01) | |
| *A01N 33/24* | (2006.01) | |
| *A01N 35/10* | (2006.01) | |
| *A01N 29/04* | (2006.01) | |

(52) U.S. Cl.
USPC ........... 424/405; 504/118; 504/141; 504/272; 504/310; 504/344; 504/356; 514/341; 514/359; 514/383; 514/640; 514/741

(58) Field of Classification Search
None
See application file for complete search history.

(56) References Cited

U.S. PATENT DOCUMENTS

| | | | |
|---|---|---|---|
| 5,972,971 A | 10/1999 | Heuer et al. | |
| 6,153,636 A | 11/2000 | Dutzmann et al. | |
| 6,306,888 B1 | 10/2001 | Zeun et al. | |
| 6,369,090 B1 | 4/2002 | Schelberger et al. | |
| 2003/0060371 A1* | 3/2003 | Asrar et al. | 504/272 |
| 2006/0100105 A1 | 5/2006 | Kober et al. | |

FOREIGN PATENT DOCUMENTS

| | | |
|---|---|---|
| DE | 19834627 | 12/1998 |
| EP | 0341954 | 3/1992 |
| EP | 0267778 | 3/1993 |
| EP | 0603845 | 12/1993 |
| EP | 0677246 | 4/1995 |
| EP | 09510831 | 6/2003 |
| JP | 04-264011 | 9/1992 |
| JP | 05-221812 | 8/1993 |
| JP | 2000-336008 | 12/2000 |
| JP | 2001-206806 | 7/2001 |
| WO | 93/24467 | 12/1993 |
| WO | 96/01054 | 1/1996 |
| WO | 96/27290 | 9/1996 |
| WO | 98/33382 | 8/1998 |
| WO | 02/37964 | 5/2002 |
| WO | 03/079787 | 10/2003 |

OTHER PUBLICATIONS

Abstract of JP2003252705 Sep. 10, 2003; 2 pages.*
Abstract of JP2003095829 Apr. 3, 2003; 2 pages.*
Database CA "Online!" Chemical Abstracts Service, Columbus, OH, US; Egawa Hitsoshi, "Wood Preservative Compositions Containing Strobilurins and Preservation Method", retrieved from STN Database accession No. 138:216834 XP002265078 *Zusammenfassung* & JP 2003 073211 A (Shinto Fine Co., Ltd., JP) Mar. 12, 2003.
Database CA "Online!" Chemical Abstracts Service, Columbus, OH, US; Egawa Hitsoshi, "Industrial antimicrobial composition containing mixed active agents", retrieved from STN Database accession No. 138:2167170 XP002265079 *Zusammenfassung* & JP 2003 095829 A (Shinto Fine Co., Ltd., JP) Apr. 3, 2003.
Database CA "Online!" Chemical Abstracts Service, Columbus, OH, US; Inui, Keiichiro et al, "Antimicrobial agents and insect repellents for wood preservation", retrieved from STN Database accession No. 139:192915 XP002265080 *Zusammenfassung* & JP 2003 252705 A (Shinto Fine Co., Ltd., JP) Sep. 10, 2003.
Database CA "Online!" Chemical Abstracts Service, Columbus, OH, US; Inui, Keiichiro et al, "Industrial antimicrobial composition containing mixed active agents", retrieved from STN Database accession No. 138:267169 XP002265081 *Zusammenfassung* & JP 2003 095828 A (Shinto Fine Co., Ltd., JP) Apr. 3, 2003.
Trifumizole Data Sheet, printed from "Alan Wood's Web site—Compendium of Pesticide Common Names," accessed on the World Wide Web at alanwood.net/pesticides/triflumizole.html, on Jan. 15, 2013.
Probenazole Data Sheet, printed from "Alan Wood's Web site—Compendium of Pesticide Common Names," accessed on the World Wide Web at alanwood.net/pesticides/probenazole.html, on Jan. 15, 2013.
Fenpropimorph Data Sheet, printed from "Alan Wood's Web site—Compendium of Pesticide Common Names," accessed on the World Wide Web at alanwood.net/pesticides/fenpropimorph.html, on Jan. 15, 2013.
Metconazole Data Sheet, printed from "Alan Wood's Web site—Compendium of Pesticide Common Names," accessed on the World Wide Web at alanwood.net/pesticides/metconazole.html, on Jan. 15, 2013.
Cinosulfuron Data Sheet, printed from "Alan Wood's Web site—Compendium of Pesticide Common Names," accessed on the World Wide Web at alanwood.net/pesticides/cinosulfuron.html, on Jan. 15, 2013.

(Continued)

*Primary Examiner* — Ernst Arnold
(74) *Attorney, Agent, or Firm* — Sterne, Kessler, Goldstein & Fox P.L.L.C.

(57) ABSTRACT

Active compound mixtures comprising ipconazole and at least one further fungicidally active compound are highly suitable for protecting industrial materials against colonization and destruction by microorganisms.

8 Claims, No Drawings

(56) References Cited

OTHER PUBLICATIONS

Triasulfuron Data Sheet, printed from "Alan Wood's Web site—Compendium of Pesticide Common Names," accessed on the World Wide Web at alanwood.net/pesticides/triasulfuron.html, on Jan. 15, 2013.
Pyrifenox Data Sheet, printed from "Alan Wood's Web site—Compendium of Pesticide Common Names," accessed on the World Wide Web at alanwood.net/pesticides/pyrifenox.html, on Jan. 15, 2013.
Fluazinam Data Sheet, printed from "Alan Wood's Web Site—Compendium of Pesticide Common Names," accessed on the World Wide Web at alanwood.net/pesticides/fluazinam.html, on Jan. 15, 2013.
Pefurazoate Data Sheet, printed from "Alan Wood's Web site—Compendium of Pesticide Common Names," accessed on the World Wide Web at alanwood.net/pesticides/pefurazoate.html, on Jan. 15, 2013.
Clodinafop-propargyl Data Sheet, printed from "Alan Wood's Web site—Compendium of Pesticide Common Names," accessed on the World Wide Web at alanwood.net/pesticides/clodinafop-propargyl.html, on Jan. 15, 2013.
Clodinafop Data Sheet, printed from "Alan Wood's Web site—Compendium of Pesticide Common Names," accessed on the World Wide Web at alanwood.net/pesticides/clodinafop.html, on Jan. 15, 2013.
Thiazopyr Data Sheet, printed from "Alan Wood's Web site—Compendium of Pesticide Common Names," accessed on the World Wide Web at alanwood.net/pesticides/thiazopyr.html, on Jan. 15, 2013.
Simazine Data Sheet, printed from "Alan Wood's Web site—Compendium of Pesticide Common Names," accessed on the World Wide Web at alanwood.net/pesticides/simazine.html, on Jan. 15, 2013.
Idosulfuron Data Sheet, printed from "Alan Wood's Web site—Compendium of Pesticide Common Names," accessed on the World Wide Web at alanwood.net/pesticides/idosulfuron.html, on Jan. 15, 2013.
Tricyclzole Data Sheet, printed from "Alan Wood's Web site—Compendium of Pesticide Common Names," accessed on the World Wide Web at alanwood.net/pesticides/tricyclazole.html, on Jan. 15, 2013.

\* cited by examiner

FUNGICIDALLY ACTIVE COMPOUND COMBINATIONS

This application is a continuation of U.S. patent application Ser. No. 11/977,086, filed Oct. 23, 2007, now abandoned, which is a continuation of U.S. patent application Ser. No. 10/688,466 filed Oct. 17, 2003, now abandoned, all incorporated herein by reference.

BACKGROUND OF THE INVENTION

1. Field of the Invention

The present invention relates to synergistic active compound mixtures comprising ipconazole and at least one further fungicidally active compound, microbicidal compositions based on these active compound mixtures and the use of these active compound mixtures, as well as compositions for protecting industrial materials.

2. Brief Description of the Prior Art

From the literature, it is known that ipconazole has fungicidal properties and can be used for protecting industrial materials (cf. EP-A 341954). However, in protecting wood and wood composites, the antifungal action of ipconazole has been found to be insufficient against all wood-destroying organisms. Accordingly, it is an object of the present invention to improve the activity of ipconazole in the protection of industrial materials, in particular wood and wood composites.

Surprisingly, it has now been found that mixtures of ipconazole with certain other fungicides have better microbicidal activity, in particular against wood-destroying organisms, compared with the activity of the sum of the individual active compounds.

SUMMARY OF THE INVENTION

Accordingly, the present invention provides novel active compound mixtures comprising
a) ipconazole of the formula (I)

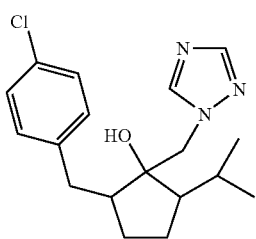

and
b) at least one further fungicidally active compound.

As can be seen from formula (I), the compounds of formula (I) can be present in the form of different stereoisomers. Accordingly, the present invention encompasses mixtures comprising the isomerically pure or isomerically enriched compounds of the formula (I) or the enantiomerically pure or enantiomerically enriched compound of the formula (I) or the racemate of the formula (I).

DETAILED DESCRIPTION OF THE INVENTION

The invention is described more fully hereunder with particular reference, but without limitation to its preferred embodiments. Preference is given to active compound mixtures according to the invention comprising, as further fungicidally active compound b), selected from the group of the metal salts or metal oxides, sulphamides, triazoles, imidazoles, benzimidazoles, morpholine derivatives, benzothiazoles, isothiazolinones, thiocyanates, quaternary ammonium compounds and guanidines, iodine derivatives, phenols, pyridines, methoxyacrylates and quinolines.

Preferred compounds b) of the mixture from the group of the metal salts and oxides are, for example, salts of the metals, copper and zinc, such as, for example, copper hydroxycarbonate, copper sulphate, copper chloride, copper borate, zinc fluorosilicate, or oxides, such as, for example, oxides of the metals copper and zinc, such as, for example, $Cu_2O$, CuO, ZnO. Preferred components b) of the mixture from the group of the sulphamides are, for example, dichlofluanid, tolylfluanid or fluorfolpet.

Preferred components b) of the mixture from the group of the triazoles are, for example, azaconazoles, bitertanol, bromuconazole, cyproconazole, epoxyconazole, fluquinconazole, hexaconazole, metconazole, penconazole, propioconazole, tebuconazole, tetraconazole or triadimenol and their metal salts and acid adducts.

Preferred components b) of the mixture from the group of the imidazoles are, for example, clotrimazole, climbazole, imazalil, ketoconazole or prochloraz and their metal salts and acid adducts.

Preferred components b) of the mixture from the group of the benzimidazoles are, for example, carbendazim or thiabendazole or their salts.

Preferred components b) of the mixture from the group of the morpholine derivatives are, for example, dodemorph, fenpropimorph, tridemorph, and their salts with arylsulphonic acids, such as, for example, p-toluenesulphonic acid and p-dodecylphenylsulphonic acid.

Preferred components b) of the mixture from the group of the benzothiazoles are, for example, 2-mercaptobenzothiazole and benzothiophenes, such as, for example, N-cyclohexyl-benzo[b]thiophenecarboxamide S,S-dioxide or bethoxazin.

Preferred components b) of the mixture from the group of the isothiazolinones are, for example, 4,5-dichloro-N-octylisothiazolin-3-one, N-octylisothiazolin-3-one or benzisothiazolinone.

Preferred components b) of the mixture from the group of the thiocyanates are, for example, thiocyanatomethylthiobenzothiazole or methylenebisthiocyanate.

Preferred components b) of the mixture from the group of the quaternary ammonium compounds and guanidines are, for example, benzalkonium chloride, benzyldimethyltetradecylammonium chloride, benzyldimethyl-dodecylammonium chloride, dichlorobenzyldimethylalkylammonium chloride, didecyldimethylammonium chloride, dioctyldimethylammonium chloride, N-hexadecyltrimethylammonium chloride, didecylmethyl-poly(oxyethyl)ammonium propionate.

Preferred components b) of the mixture from the group of the iodine derivatives are, for example, diiodomethyl-p-tolyl sulphone or 3-iodo-2-propynyl n-butylcarbamate.

Preferred components b) of the mixture from the group of the phenols are, for example, tribromophenol, 3-methyl-4-chlorophenol, 3,5-dimethyl-4-chlorophenol, dichlorophen, 2-benzyl-4-chlorophenol, triclosan, diclosan, hexachlorophen, p-hydroxybenzoic esters, o-phenylphenol and their alkali metal and alkaline earth metal salts.

Preferred components b) of the mixture from the group of the pyridines are, for example, 1-hydroxy-2-pyridinethione (and its Cu, Na, Fe, Mn, Zn salts) or tetrachloro-4-methylsulphonylpyridine.

Preferred components b) of the mixture from the group of the methoxyacrylates are, for example, azoxystrobin or trifloxystrobin.

Preferred components b) of the mixture from the group of the quinolines are, for example, quinoxyfen, 8-hydroxyquinoline and their Cu salts. Particularly preferred are mixtures of a) ipconazole of the formula (I) with at least one fungicidally active compound b) from the group consisting of:

azaconazole, cyproconazole, fluquinconazole, hexaconazole, propioconazole, tebuconazole, triadimenol, climbazole, imazalil, prochloraz, dichiofluanid, tolylfluanid, thiabendazole, fenpropimorph, tridemorph, N-cyclohexyl-benzo[b]thiophenecarboxamide S,S-dioxide, bethoxazin, thiocyanatomethylthiobenzothiazole, benzalkonium chloride, didecyldimethylammonium chloride, didecylmethylpoly(oxyethyl)-ammonium propionate, 3-iodo-2-propynyl butylcarbamate, and trifloxystrobin.

Especially preferred are mixtures of a) ipconazole of the formula (I) with at least one fungicidally action compound b) selected from the group consisting of:

cyproconazole, fluquinconazole, tebuconazole, triadimenol, prochloraz, tolylfluanid, bethoxazin, benzalkonium chloride, didecyldimethylammonium chloride, didecyl-methylpoly(oxyethyl)ammonium propionate, 3-iodo-2-propynyl butylcarbamate.

The weight ratios of the active compounds a) and b) in the active compound mixture according to the invention can be varied within a relatively wide range.

However, if the active compounds a) and b) in the active compound mixtures according to the invention are present in certain weight ratios, the synergistic effect is particularly pronounced. Accordingly, the present invention provides active compound mixtures comprising a synergistically effective amount of a) ipconazole of the formula (I) and a synergistically effective amount of at least one further fungicidally active compound b). Preferred are weight ratios of fungicidally active compound b) to a) ipconazole of from 1:20 to 20:1, particularly preferably from 1:4 to 4:1.

If appropriate, the mixtures according to the invention may additionally comprise one or more of the following active compounds c):

Insecticides:
acetamiprid, allethrin, alpha-cypermethrin, beta-cyfluthrin, bifenthrin, bioallethrin, 4-chloro-2-(2-chloro-2-methyl-propyl)-5-[(6-iodo-3-pyridinyl) methoxy]-3(2H)-pyridazinone (CAS-RN: 120955-77-3), chlorfenapyr, chlorpyrifos, clothianidin, cyfluthrin, cyhalothrin, cypermethrin, deltamethrin, ethofenprox, fenoxycarb, fipronil, flufenoxuron, hexaflumuron, imidacloprid, nitenpyram, permethrin, pyriproxifen, silafluofen, tebufenozide, thiamethoxam, tralomethrin, triflumuron;

Algicides:
benzthiazuron, cybutrin, difenoxuron, diuron, dazomet, ethoxyfen, fluometuron, methabenzthiazuron, terbutryn.

Preference is given to active compound mixtures according to the invention comprising, as further active compound c), at least one of the following insecticides and/or algicides:

alpha-cypermethrin, bifenthrin, chlorfenapyr, clothianidin, cyfluthrin, cypermethrin, deltamethrin, fipronil, imidacloprid, permethrin, cybutrin, diuron, terbutryn.

Particular preference is given to active compound mixtures according to the invention which, as further active compound c), comprise at least one of the following insecticides:

alpha-cypermethrin, bifenthrin, chlorfenapyr, cypermethrin, fipronil, imidacloprid, permethrin;

In the active compound mixture according to the invention, the active compounds c) are generally present in an amount of from 0.00001% by weight to 10% by weight, preferably from 0.0001% by weight to 5% by weight and particularly preferably from 0.001% by weight to 1% by weight.

The active compound mixtures according to the invention can be prepared by mixing the individual components a) and b) and, if appropriate, c) with one another in a customary manner, if appropriate with addition of solvents and processing auxiliaries.

The active compound mixtures according to the invention have strong microbicidal action and can be used for controlling microorganisms, such as, for example, fungi, bacteria and algae, in the protection of materials. The active compound combinations are preferably used for controlling microorganisms in the protection of wood.

In the protection of materials, the active compound combinations according to the invention can be used for protecting industrial materials against colonization and destruction by microorganisms.

The present invention furthermore provides the use of the mixtures according to the invention as microbicide for protecting industrial materials.

In the present context, industrial materials are to be understood as meaning non-living materials which have been prepared for use in industry. The industrial materials are, for example, adhesives, sizes, paper and board, textiles, leather, wood, woodbased materials, paints and plastic articles, cooling lubricants and other materials which can be colonized or destroyed by microorganisms. Furthermore, in the context of the present invention, industrial materials are also to be understood as meaning parts of production plants, for example cooling-water circuits, which may be impaired by the proliferation of microorganisms. Industrial materials which are preferably protected are adhesives, sizes, paper and board, leather, wood, woodbased materials, paints, plastic articles, cooling lubricants and heat-transfer liquids.

The active compound combinations according to the invention are particularly suitable for protecting wood, woodbased materials, plastics, cooling lubricants and coating systems, such as paints, varnishes or plaster, against colonization by microorganisms. The active compound combinations according to the invention are particularly preferably suitable for protecting wood, woodbased materials, plastics and coating systems, such as paints, varnishes or plaster, against colonization by microorganisms.

Microorganisms capable of degrading or changing the industrial materials which may be mentioned are, for example, bacteria, fungi, yeasts, algae and slime organisms. The active compound combinations according to the invention preferably act against fungi, in particular moulds, wood-discolouring and wood-destroying fungi (Basidiomycetes) and insects and against slime organisms and algae. Especially preferred is the action of the active compound combinations against wood-destroying fungi and insects.

Wood which can be protected by the active compound combinations according to the invention or compositions comprising them is to be understood as meaning, for example: construction timber, wooden beams, railway sleepers, bridge components, jetties, wooden vehicles, boxes, pallets, containers, telephone poles, wooden claddings, windows and doors made from wood, plywood, chipboard, joiner's wood or woodbased materials which are quite generally used in domestic construction or in joinery.

Particularly effective protection of wood is achieved by industrial-scale impregnating processes, for example vacuum, double-vacuum or pressure processes.

The synergistic combinations claimed have particularly high microbicidal, in particular fungicidal, action, together with a broad activity spectrum against microorganisms encountered in the protection of materials; they are particularly effective against moulds, wood-discolouring and wood-destroying fungi.

The following groups of microorganisms may be mentioned by way of example, but not by way of limitation:

A. Wood-discolouring fungi:
  A1: Ascomycetes
    *Ceratocystis*, such as *Ceratocystis minor*
  A2: Deuteromycetes:
    *Aspergillus*, such as *Aspergillus niger*
    *Aureobasidium*, such as *Aureobasidium pullulans*
    *Dactylium*, such as *Dactylium fusarioides*
    *Penicillium*, such as *Penicillium brevicaule* or
    *Penicillium variabile*
    *Sclerophoma*, such as *Sclerophoma pithyophila*
    *Scopularia*, such as *Scopularia phycomyces*
    *Trichoderma*, such as *Trichoderma viride* or
    *Trichoderma lignorum*
  A3: Zygomycetes:
    *Mucor*, such as *Mucor spinorus*
  Wood-destroying fungi:
  B1: *Chaetomium*, such as *Chaetomium globosum* or
    *Chaetomium alba-arenulum*
    *Humicola grisea*
    *Petriella*, such as *Petriella setifera*
    *Trichurus*, such as *Trichurus spiralis*
  B2: Basidiomycetes
    *Coniophora*, such as *Coniophora puteana*
    *Coriolus*, such as *Coriolus versicolor*
    *Donkioporia*, such as *Donkioporia expans*
    *Glenospora*, such as *Glenospora graphii*
    *Gloeophyllum*, such as *Gloeophyllum abietinum* or
    *Gloeophyllum adoratum* or
    *Gloeophyllum protactum* or
    *Gloeophyllum sepiarium* or
    *Gloeophyllum trabeum*
    *Lentinus*, such as *Lentinus cyathiformes* or
    *Lentinus edodes* or
    *Lentinus lepideus* or
    *Lentinus grinus* or
    *Lentinus squarrolosus*
    *Paxillus*, such as *Paxillus panuoides*
    *Pleurotus*, such as *Pleurotus ostreatus*
    *Poria*, such as *Poria monticola* or
    *Poria placenta* or
    *Poria vaillantii* or
    *Poria vaporaria*
    *Serpula*, such as *Serpula himantoides* or
    *Serpula lacrymans*
    *Stereum*, such as *Stereum hirsutum*
    *Tyromyces*, such as *Tyromyces palustris*

The combinations according to the invention are highly suitable for protecting wood and woodbased materials against attack by wood-destroying insects, such as, for example, 1. Beetles
*Hylotrupes bajulus, Chlorophorus pilosis, Anabium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus*

2. *Hymenoptera*
*Sirex juvencus, Urocerus gigas, Urocerus gigas taignus, Urocerus augur*

3. Termites
*Kalotermes flavicollis, Cryptotermes brevis, Heterotermes indicola, Reticulitermes flavipes, Reticulitermes santonensis, Reticulitermes lucilugus, Mastotermes darwiniensis, Zootermopsis nevadensis, Coptotermes formosanus*

Depending on their particular physical and/or chemical properties, the active compound mixtures can be converted into the customary formulations, such as solutions, emulsions, suspensions, powders, foams, pastes, granules, aerosols and microencapsulations in polymeric substances.

These formulations can be produced in a known manner, for example by mixing the active compound mixture or the individual active compounds a) and b) and, if appropriate, c) with extenders, that is liquid solvents, liquefied gases under pressure and/or solid carriers, if appropriate with the use of surfactants, that is emulsifiers and/or dispersants and/or foam-formers. If the extender used is water, it is also possible to employ, for example, organic solvents as auxiliary solvents. Essentially, suitable liquid solvents are: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol and their ethers and esters, ketones, such as acetone, methyl ethyl ketone, methyl isobutyl ketone or cyclohexanone, strongly polar solvents, such as dimethylformamide and dimethyl sulphoxide, and also water. Liquefied gaseous extenders or carriers are to be understood as meaning liquids which are gaseous at standard temperature and under atmospheric pressure, for example aerosol propellants, such as halogenated hydrocarbons, and also butane, propane, nitrogen and carbon dioxide.

Suitable solid carriers are: for example ground natural minerals, such as kaolins, clays, talc, chalk, quartz, attapulgite, montmorillonite or diatomaceous earth, and ground synthetic minerals, such as finely divided silica, alumina and silicates. Suitable solid carriers for granules are: for example crushed and fractionated natural rocks, such as calcite, marble, pumice, sepiolite and dolomite, and also synthetic granules of inorganic and organic meals, and granules of organic materials such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, and also protein hydrolysates. Suitable dispersants are, for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use colorants, such as inorganic pigments, for example iron oxide, titanium oxide and Prussian Blue and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95% by weight of active compound mixture, preferably between 0.5 and 25% by weight.

The present invention furthermore provides microbicidal compositions based on the active compound combinations according to the invention, which compositions comprise at least one solvent or diluent and, if appropriate, processing auxiliaries and, if appropriate, further antimicrobially active compounds.

The microbicidal compositions or concentrates used for protecting the industrial materials comprise the active compound mixture according to the invention in a concentration of from 0.01 to 95% by weight, in particular from 0.1 to 25% by weight.

The concentrations of the active compound mixture to be used according to the invention depend on the nature and the occurrence of the microorganisms to be controlled and on the composition of the material to be protected. The optimum application rate can be determined by test series. In general, the use concentrations are in the range of from 0.001 to 5% by weight, preferably from 0.01 to 1.5% by weight, based on the material to be protected.

The active compound mixtures or compositions according to the invention have, compared to the microbicidal compositions known from the prior art, improved microbicidal activity, Furthermore, they have good stability and cover, in an advantageous manner, a broad activity spectrum.

The active compound mixtures can be used as such, in the form of their formulations or the use forms prepared therefrom, such as ready-to-use solutions, suspensions, pastes, soluble powders. The application is carried out in a customary manner, for example by spraying, spreading, dipping and industrial impregnation processes, for example vacuum, double-vacuum or pressure processes.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. An active compound mixture, comprising
a) ipconazole of the formula (I)

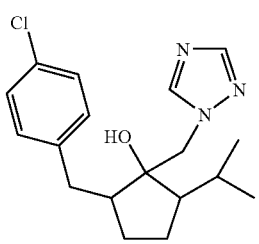

(I)

and b) at least one further fungicidally active compound, wherein the further fungicidally active compound is a methoxyacrylate, wherein the methoxyacrylate is trifloxystrobin or azoxystrobin;

characterized in that the weight ratio of the fungicidally active compound b) to ipconazole a) is from 1:20 to 20:1.

2. An active compound mixture, comprising
a) ipconazole of the formula (I)

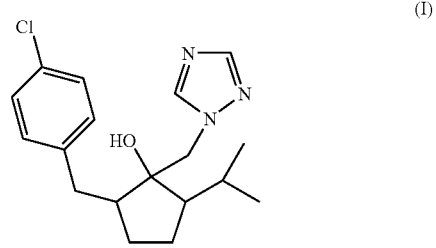 [SMILES: CC(C)C1CCC(Cc2ccc(Cl)cc2)C1(O)Cn1cncn1]

(I)

and b) at least one further fungicidally active compound, wherein the further fungicidally active compound is a methoxyacrylate, wherein the methoxyacrylate is trifloxystrobin or azoxystrobin and c) at least one further active compound c) from the group of the insecticides and/or algicides;

characterized in that the weight ratio of the fungicidally active compound b) to ipconazole a) is from 1:20 to 20:1.

3. A method for protecting industrial materials comprising:

applying to the industrial materials a compound mixture, comprising:

a) ipconazole of the formula (I)

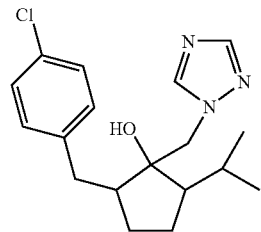

(I)

and b) at least one further fungicidally active compound, wherein the further fungicidally active compound is a methoxyacrylate, wherein the methoxyacrylate is trifloxystrobin or azoxystrobin;

characterized in that the weight ratio of the fungicidally active compound b) to ipconazole a) is from 1:20 to 20:1.

4. The method according to claim 3, wherein the industrial materials are wood, woodbased materials, plastics, cooling lubricants, coating systems, paints varnishes, or plasters.

5. A method for protecting industrial materials against colonization and/or destruction by micro-organisms comprising:

allowing a compound mixture to act on the micro-organism or its habitat, wherein said compound mixture comprises:

a) ipconazole of the formula (I)

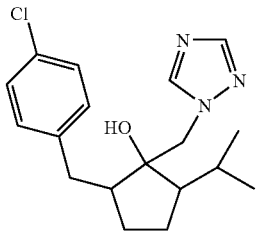

and
b) at least one further fungicidally active compound, wherein the further fungicidally active compound is a methoxyacrylate, wherein the methoxyacrylate is trifloxystrobin or azoxystrobin;

characterized in that the weight ratio of the fungicidally active compound b) to ipconazole a) is from 1:20 to 20:1.

6. A microbicidal composition, comprising the active compound mixture according to claim 1 further comprising at least one of the following, a solvent, a diluent, a processing auxiliary, and/or a further antimicrobially active compound.

7. The microbicidal composition according to claim 6, further comprising at least one algicide and/or insecticide.

8. An industrial material comprising:
a) ipconazole of the formula (I)

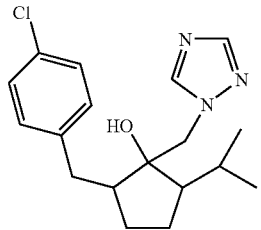

and
b) at least one further fungicidally active compound, wherein the further fungicidally active compound is a methoxyacrylate, wherein the methoxyacrylate is trifloxystrobin or azoxystrobin;

characterized in that the weight ratio of the fungicidally active compound b) to ipconazole a) is from 1:20 to 20:1.

* * * * *